US00PP09009P

United States Patent [19]

Austin

[11] Patent Number: Plant 9,009

[45] Date of Patent: Dec. 13, 1994

[54] SHRUB ROSE PLANT NAMED AUSDIR

[75] Inventor: David C. H. Austin, Albrighton, England

[73] Assignee: David Austin Roses Limited, Albrighton, England

[21] Appl. No.: 182,788

[22] Filed: Jan. 13, 1994

[51] Int. Cl.[5] ..... A01N 5/00

[52] U.S. Cl. ..... Plt./1

[58] Field of Search ..... Plt. 1, 29

*Primary Examiner*—Howard J. Locker
*Attorney, Agent, or Firm*—Klarquist Sparkman Campbell Leigh & Whinston

[57] ABSTRACT

A shrub rose having red-purple, old-fashioned-shaped flowers; spreading growth; and repeat flowering.

1 Drawing Sheet

The present invention relates to a new and distinct variety of rose plant of the shrub class which was originated by me by crossing the variety "Prospero" with an unnamed seedling.

The primary objective of this breeding was to produce a new shrub rose variety that is repeat flowering and has red, old-fashioned-type flowers. The objective was substantially achieved, along with other desirable improvements, as evidenced by the following unique combination of characteristics that are outstanding in the new variety and that distinguish it from its parents, as well as from all other varieties of which I am aware:

1. Deep red to red-purple flowers;
2. Spreading growth;
3. Old-fashioned shape of flower; and
4. Repeat-flowering.

Asexual reproduction of this new variety by budding, as performed at Albrighton, Wolverhampton, England, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—"Prospero" (unpatented).

*Pollen parent.*—Unnamed seedling.

Classification:

*Botanical.*—Rosa hybrida.

*Commercial.*—Shrub.

FLOWER

Observations made from specimens grown in a garden environment at Albrighton, Wolverhampton, England, in July 1992.

Blooming habit: Recurrent.

Bud:

*Size.*—About 2 cm long when the petals start to unfurl.

*Form.*—The bud form is short, pointed ovoid.

*Color.*—When sepals first divide, bud color is Red-Purple Group 59A. When half blown, the upper sides of the petals are Red-Purple Group 59A to 60A; and the lower sides of the petals are Red-Purple Group 60A.

*Sepals.*—Color: Yellow-Green Group 144A/B. Surface texture: Glabrous, or with occasional fine, white downy hairs. There are three lightly appendaged sepals. There are two unappendaged sepals with hairy edges.

*Receptacle.*—Color: Yellow-Green Group 144A/B/C with Greyed-Red Group 181B blush. Shape: Goblet shaped. Size: About 8 mm×9 mm. Surface: Smooth.

*Peduncle.*—Length: Averaging about 3.8 cm. Surface: Glandular. Color: Bronzy. Strength: Stiff, erect.

Bloom:

*Size.*—Average open diameter is 6.5 cm.

*Borne.*—In irregularly shaped clusters of 3 to 18 blooms.

*Stems.*—Average length is about 65 to 80 cm.; normal strength.

*Form.*—When first open: Bloom is cupped. Permanence: Flattens to form quartered rosette. Outer petals curl back.

*Petalage.*—Number of petals under normal conditions: 120.

*Color.*—The upper side of the petals is Red-Purple Group 59B. The reverse side of the petals is Red-Purple Group 60B. The tip of the base of each petal is Yellow Group 9A/B/C or D. The major color on the upper side is Red-Purple Group 59B.

*Variegations.*—None.

*Discoloration.*—The general tonality at the end of the first day: Red-Purple Group 61A. At the end of the third day, Greyed-Purple Group 187A.

*Fragrance.*—Moderate to strong; very sweet.

Petals:

*Texture.*—Thick.

*Shape.*—Outer: heart-shaped/deltoid, apex notched, edges quilled. Inner: more ovoid, apex pointed, folded lengthwise.

*Form.*—Edges slightly quilled.

*Arrangement.*—Quartered (center); regularly arranged, shingle-like, inner petals tucked into calyx, with few petaloids in the center.

*Persistence.*—Petals tend to hang on and dry.

*Lastingness.*—On the plant: About 4 to 5 days. As a cut flower: About 4 days.

Reproductive parts:

*Anthers.*—Size: Small to medium. Quantity: Few. Color: Reddish yellow. Arrangement: Partly tucked into calyx; mixed with petaloids.

*Filaments.*—Color: Red-Purple Group 67A.

*Pollen.*—Color: Gold yellow.

*Styles:* Color: Greenish white with Red-Purple Group

*Stigmas.*—Color: Greenish white.

Form: Shrub.

Growth: Vigorous. Mature plant about 190 cm in height and width.

Foliage: Number of leaflets on normal mid-stem leaves: 5.

*Size.*—About 16 cm long × 12 to 13 cm wide.

*Quantity.*—Normal.

*Color.*—New foliage: Yellow-Green Group 146A with Red-Purple Group 59A. blush on margins. Old foliage: Yellow-Green Group 146A/147A.

Leaflets:

*Shape.*—Pointed oval.

*Texture.*—Upper side: Leathery.

*Edge.*—Serrated.

*Serration.*—Slightly double or single; small.

*Petiole rachis.*—Color: Reddish.

*Petiole underside.*—0 to 2 prickles per internode.

*Stipules.*—Finely serrated, glandular edges; about 2.0 to 2.5 cm long.

*Disease resistance.*—Resistant to mildew and black-spot under normal growing conditions at Albrighton, Wolverhampton, England.

Wood:

*New wood.*—Color: Reddish. Bark: Smooth.

*Old wood.*—Color: Green. Bark: Smooth.

Prickles:

*Quantity.*—On main canes from base: Ordinary to many. On laterals from main canes: Ordinary.

*Form.*—Medium length; straight or slightly hooked downward.

*Color when young.*—Reddish, tips transparent.

*Position.*—Randomly distributed on stems.

Small prickles:

*Quantity.*—On main stalks: Few. On laterals: None.

*Color.*—Brown.

I claim:

1. A new and distinct variety of rose plant of the shrub class, substantially as herein shown and described, characterized particularly as to novelty by the unique combination of its red-purple, old-fashioned-shaped flowers, spreading growth, and repeat flowering.

* * * * *

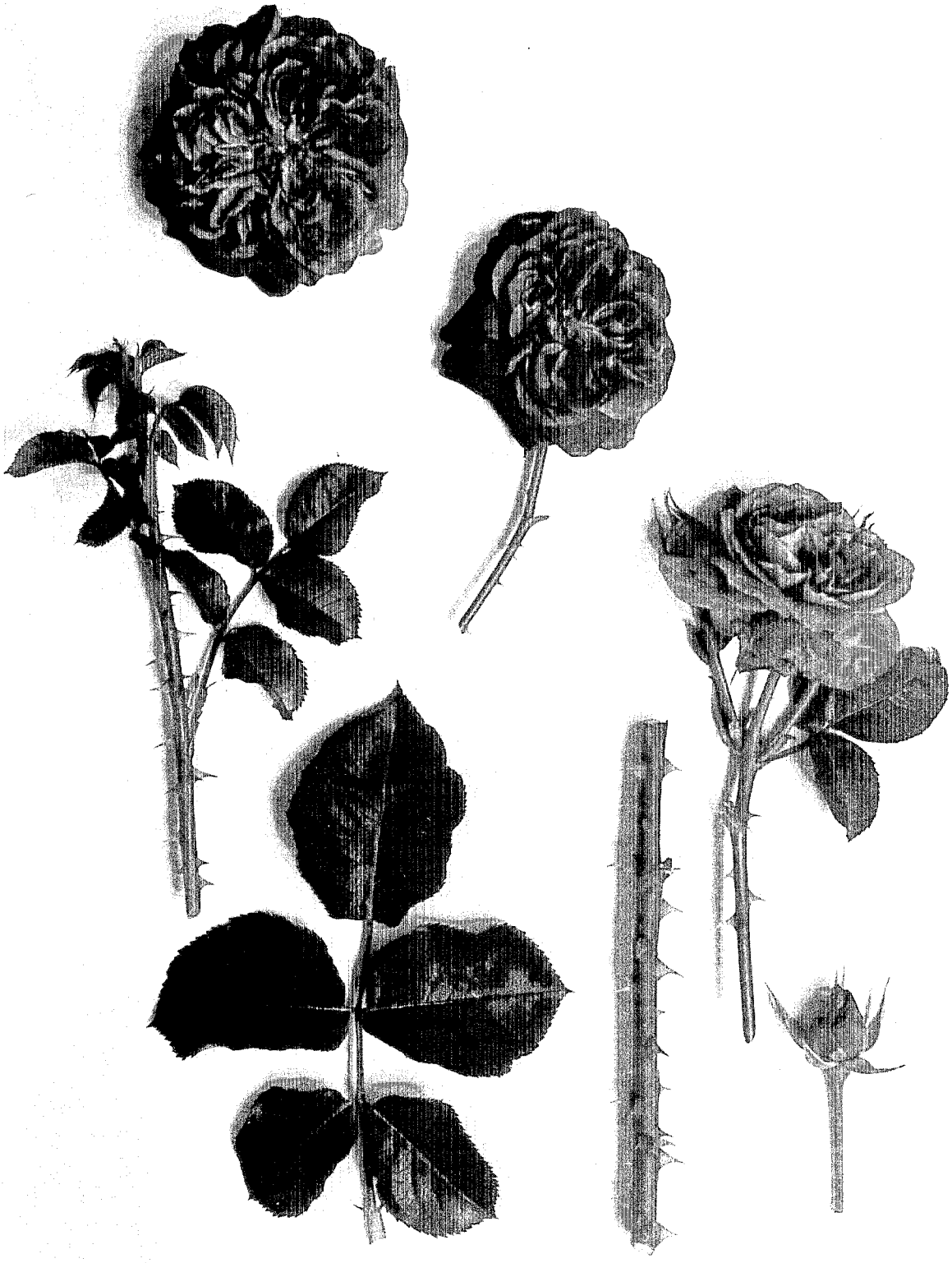

UNITED STATES PATENT AND TRADEMARK OFFICE

CERTIFICATE OF CORRECTION

PATENT NO. : PP 9,009

DATED : December 13, 1994

INVENTOR(S) : David C. H. Austin

It is certified that error appears in the above-identified patent and that said Letters Patent is hereby corrected as shown below:

Column 3, line 13, "190 cm" should be changed to --75 cm--.

Signed and Sealed this

Sixth Day of May, 1997

*Attest:*

Bruce Lehman

BRUCE LEHMAN

*Attesting Officer*

*Commissioner of Patents and Trademarks*